United States Patent
Kreeger et al.

(10) Patent No.: US 10,573,276 B2
(45) Date of Patent: *Feb. 25, 2020

(54) SYSTEM AND METHOD FOR GENERATING A 2D IMAGE USING MAMMOGRAPHY AND/OR TOMOSYNTHESIS IMAGE DATA

(71) Applicant: HOLOGIC, INC., Marlborough, MA (US)

(72) Inventors: Kevin Kreeger, Sunnyvale, CA (US); Andrew P. Smith, Lexington, MA (US); Ashwini Kshirsagar, Cupertino, CA (US); Jun Ge, Cupertino, CA (US); Yiheng Zhang, Reading, MA (US); Haili Chui, Fremont, CA (US); Christopher Ruth, Boxford, MA (US); Xiangwei Zhang, Fremont, CA (US); Liyang Wei, San Jose, CA (US); Jay Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/013,701

(22) Filed: Jun. 20, 2018

(65) Prior Publication Data

US 2019/0043456 A1   Feb. 7, 2019

Related U.S. Application Data

(63) Continuation of application No. 14/360,389, filed as application No. PCT/US2012/066526 on Nov. 26, 2012, now Pat. No. 10,008,184.

(Continued)

(51) Int. Cl.
*G09G 5/377* (2006.01)
*G06T 11/00* (2006.01)
*G06T 7/30* (2017.01)

(52) U.S. Cl.
CPC ............... *G09G 5/377* (2013.01); *G06T 7/30* (2017.01); *G06T 11/006* (2013.01);
(Continued)

(58) Field of Classification Search
CPC .......... G09G 5/377; G06T 2207/20221; G06T 2207/30068; G06T 5/50
See application file for complete search history.

(56) References Cited

U.S. PATENT DOCUMENTS

| 3,502,878 A | 3/1970 | Stewart et al. |
| 3,863,073 A | 1/1975 | Wagner |

(Continued)

FOREIGN PATENT DOCUMENTS

| DE | 102010009295 | 8/2011 |
| EP | 775467 | 5/1997 |

(Continued)

OTHER PUBLICATIONS

Office action dated Aug. 27, 2018 for U.S. Appl. No. 15/794,635.

(Continued)

*Primary Examiner* — Jeffery A Brier
(74) *Attorney, Agent, or Firm* — Vista IP Law Group, LLP

(57) ABSTRACT

The invention includes a method including the steps of obtaining a plurality of images, each of the images in the plurality having at least one corresponding region, generating a merged image, the merged image also having the corresponding region. The step of generating includes selecting an image source from the plurality of images to source image data for the corresponding region in the merged image by comparing attributes of the corresponding regions of the plurality of images to identify the image source having preferred attributes.

13 Claims, 7 Drawing Sheets

Related U.S. Application Data

(60) Provisional application No. 61/563,785, filed on Nov. 27, 2011.

(52) U.S. Cl.
CPC .. *G06T 11/008* (2013.01); *G06T 2207/10081* (2013.01); *G06T 2207/20221* (2013.01); *G06T 2207/30068* (2013.01); *G06T 2211/436* (2013.01)

(56) References Cited

U.S. PATENT DOCUMENTS

| | | | |
|---|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 3/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,712,890 A | 1/1998 | Spivey et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz |
| 5,872,828 A | 2/1999 | Niklason |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,986,662 A | 11/1999 | Argiro |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,272,207 B1 | 8/2001 | Tang |
| 6,289,235 B1 | 9/2001 | Webber et al. |
| 6,292,530 B1 | 9/2001 | Yavus |
| 6,327,336 B1 | 12/2001 | Gingold et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,442,288 B1 | 8/2002 | Haerer |
| 6,459,925 B1 | 10/2002 | Nields et al. |
| 6,463,181 B2 | 10/2002 | Duarte |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,912,319 B1 | 5/2005 | Barnes |
| 6,940,943 B2 | 9/2005 | Claus |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |
| 7,127,091 B2 | 10/2006 | OpDeBeek |
| 7,142,633 B2 | 11/2006 | Eberhard |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,702,142 B2 | 4/2010 | Ren et al. |
| 7,760,924 B2 | 7/2010 | Ruth et al. |
| 7,831,296 B2 | 11/2010 | DeFreitas et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,571,289 B2 | 10/2013 | Ruth |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,084,579 B2 | 7/2015 | Ren et al. |
| 9,456,797 B2 | 10/2016 | Ruth et al. |
| 9,805,507 B2 | 10/2017 | Chen |
| 9,808,215 B2 | 11/2017 | Ruth et al. |
| 9,811,758 B2 | 11/2017 | Ren et al. |
| 1,000,818 A1 | 6/2018 | Kreeger et al. |
| 10,008,184 B2 * | 6/2018 | Kreeger ............ G06T 11/006 |
| 1,001,030 A1 | 7/2018 | Ruth et al. |

(56) References Cited

U.S. PATENT DOCUMENTS

| | | |
|---|---|---|
| 1,041,041 A1 | 9/2019 | Chen et al. |
| 1,041,326 A1 | 9/2019 | Ruth et al. |
| 2001/0038861 A1 | 11/2001 | Hsu et al. |
| 2002/0012450 A1 | 1/2002 | Tsujii |
| 2002/0050986 A1 | 5/2002 | Inoue |
| 2002/0075997 A1 | 6/2002 | Unger et al. |
| 2003/0007598 A1 | 1/2003 | Wang |
| 2003/0018272 A1 | 1/2003 | Treado et al. |
| 2003/0026386 A1 | 2/2003 | Tang |
| 2003/0073895 A1 | 4/2003 | Nields et al. |
| 2003/0095624 A1 | 5/2003 | Eberhard et al. |
| 2003/0128893 A1 | 7/2003 | Castorina et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008901 A1 | 1/2004 | Avinash |
| 2004/0047518 A1 | 3/2004 | Tiana |
| 2004/0052328 A1 | 3/2004 | Saboi |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0135555 A1 | 6/2005 | Claus et al. |
| 2005/0135664 A1 | 6/2005 | Kaufhold |
| 2005/0226375 A1 | 10/2005 | Eberhard |
| 2006/0018526 A1 | 1/2006 | Avinash |
| 2006/0030784 A1 | 2/2006 | Miller et al. |
| 2006/0074288 A1 | 4/2006 | Kelly et al. |
| 2006/0098855 A1 | 5/2006 | Gkanatsios |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0052700 A1 | 3/2007 | Wheeler et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0045833 A1 | 2/2008 | Defreitas et al. |
| 2008/0130979 A1 | 6/2008 | Ren |
| 2008/0187095 A1 | 8/2008 | Boone et al. |
| 2009/0003519 A1 | 1/2009 | Defreitas et al. |
| 2009/0005668 A1 | 1/2009 | West et al. |
| 2009/0010384 A1 | 1/2009 | Jing et al. |
| 2009/0034684 A1 | 2/2009 | Bernard et al. |
| 2009/0080594 A1 | 3/2009 | Brooks et al. |
| 2009/0080602 A1 | 3/2009 | Brooks et al. |
| 2009/0080765 A1 | 3/2009 | Bernard et al. |
| 2009/0123052 A1 | 5/2009 | Ruth et al. |
| 2009/0135997 A1 | 5/2009 | Defreitas et al. |
| 2009/0238424 A1 | 9/2009 | Arakita et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0086188 A1 | 4/2010 | Ruth et al. |
| 2010/0135558 A1 | 6/2010 | Ruth et al. |
| 2010/0195882 A1 | 8/2010 | Ren et al. |
| 2010/0259645 A1 | 10/2010 | Kaplan |
| 2011/0069906 A1 | 3/2011 | Park |
| 2011/0109650 A1 | 5/2011 | Kreeger et al. |
| 2011/0110576 A1 | 5/2011 | Kreeger et al. |
| 2011/0178389 A1 | 7/2011 | Kumar et al. |
| 2011/0234630 A1 | 9/2011 | Batman et al. |
| 2011/0242092 A1 | 10/2011 | Kashiwagi |
| 2012/0293511 A1 | 11/2012 | Mertelmeier |
| 2013/0121569 A1* | 5/2013 | Yadav ................. G06T 5/50 382/164 |
| 2013/0121618 A1* | 5/2013 | Yadav ................. G06T 5/008 382/294 |
| 2014/0327702 A1 | 11/2014 | Kreeger et al. |
| 2015/0317538 A1 | 11/2015 | Ren et al. |
| 2018/0047211 A1 | 2/2018 | Chen et al. |
| 2018/0137385 A1 | 5/2018 | Ren |

FOREIGN PATENT DOCUMENTS

| | | |
|---|---|---|
| EP | 982001 | 3/2000 |
| EP | 1428473 | 6/2004 |
| EP | 2215600 | 8/2010 |
| EP | 2301432 | 3/2011 |
| JP | 2003-189179 | 7/2003 |
| JP | 2007-536968 | 12/2007 |
| JP | 2009-207545 | 9/2009 |
| WO | WO 90/05485 | 5/1990 |
| WO | WO 9816903 | 4/1998 |
| WO | WO 00/51484 | 9/2000 |
| WO | WO 03020114 | 3/2003 |
| WO | WO 2005051197 | 6/2005 |
| WO | WO 2005110230 | 11/2005 |
| WO | WO 2005112767 | 12/2005 |
| WO | WO 2006055830 | 5/2006 |
| WO | WO 2006058160 | 6/2006 |
| WO | WO 2008047270 | 4/2008 |
| WO | WO 2010059920 | 5/2010 |
| WO | WO 2011008239 | 1/2011 |
| WO | WO 2011065950 | 6/2011 |
| WO | WO 2011073864 | 6/2011 |
| WO | WO 2011091300 | 7/2011 |
| WO | WO 2012063653 | 5/2012 |

OTHER PUBLICATIONS

Amendment response to office action filed Nov. 14, 2018 for U.S. Appl. No. 15/794,635.

Notice of Allowance dated Jan. 17, 2019 for U.S. Appl. No. 15/794,635.

Non Final office Action dated Jan. 25, 2019 for U.S. Appl. No. 16/013,782.

European search report in connection with corresponding European patent application No. EP 06255790, dated Aug. 17, 2007.

European search report in connection with counterpart European Patent Application No. 05824734, dated May 9, 2011.

PCT International Search Report and Written Opinion dated Sep. 25, 2008, for International Application No. PCT/US2005/041941, Applicant Hologic, Inc., 8 pages.

Amendment After Non-Final Office Action filed Apr. 12, 2019 for U.S. Appl. No. 16/013,782.

Non Final Office Action dated Sep. 21, 2016 for U.S. Appl. No. 14/744,930.

Response to Non Final Office action filed Dec. 14, 2016 for U.S. Appl. No. 14/744,930.

Final Office Action dated Mar. 31, 2017 for U.S. Appl. No. 14/744,930.

Response to Final Office action filed Aug. 2, 2017 for U.S. Appl. No. 14/744,930.

Non Final Office action dated May 18, 2018 for U.S. Appl. No. 15/804,915.

Response to Non Final Office Action filed Aug. 20, 2018 for U.S. Appl. No. 15/804,915.

Mikko Lilja, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway NJ, Oct. 25, 2008.

(56) References Cited

OTHER PUBLICATIONS

Pediconi, "Color-coded automated signal intensity-curve for detection and characterization of breast lesions: Preliminary evaluation of new software for MR-based breast imaging," International Congress Series 1281 (2005) 1081-1086.
Heang-Ping, ROC "Study of the effect of stereoscopic imaging on assessment of breast lesions," Medical Physics, vol. 32, No. 4, Apr. 2005.
Amendment Response to Final Office Action for U.S. Appl. No. 12/276,006 dated Mar. 24, 2010 (6 pages).
Amendment Response to Non-Final Office Action for U.S. Appl. No. 12/276,006 dated Sep. 28, 2009 (8 pages).
Final Office Action dated Jan. 20, 2010 for U.S. Appl. No. 12/276,006.
Non-Final Office Action dated Jun. 25, 2009 for U.S. Appl. No. 12/276,006.
Amendment Resonse after Final Office Action for U.S. Appl. No. 12/471,981 dated Apr. 3, 2013 (6 pages).
Amendment Response to Non-Final Office Action for U.S. Appl. No. 12/471,981 dated Dec. 10, 2012 (6 pages).
Non-Final Office Action dated Feb. 13, 2013 for U.S. Appl. No. 12/471,981.
Non-Final Office Action dated Aug. 10, 2012 for U.S. Appl. No. 12/471,981.
Amendment Response to Non-Final Office Action for U.S. Appl. No. 14/044,959 dated May 13, 2014 (8 pages).
Non-Final Office Action dated Feb. 13, 2014 for U.S. Appl. No. 14/044,959.
Foreign Office Action for CN Application No. 200980101409.X dated Jun. 26, 2014.
Foreign Office Action for EP Patent Application No. 09796173.4 dated Apr. 11, 2014.
Foreign Office Action for JP Patent Application No. 2011-537644 dated Jul. 29, 2013.
Foreign Office Action for JP Patent Application No. 2014-047021 dated Jan. 21, 2015.
International Search Report for International Publication No. PCT/US2009/065288 dated Jan. 29, 2014.
International Preliminary Report on Patentability for International Publication No. PCT/US2012/066526 dated May 27, 2014.
PCT Notification of International Search Report and Written Opinion for PCT/US2012/066526, Applicant Hologic, Inc., dated Feb. 6, 2013 (7 pages).
International Preliminary Report on Patentability for International Publication No. PCT/US2013/025993 dated Aug. 19, 2014.
International Search Report and Written Opinion for International Publication No. PCT/US2013/025993 dated Apr. 26, 2013.
Foreign office action from JP 2014-543604 dated Oct. 4, 2016.
Extended EP Search Report for EP Application No. 13749870.5 dated Oct. 7, 2015, 7 pages.
Extended EP Search Report for EP Application No. 12851085.6, dated Jan. 6, 2015, 6 pages.
Giger et al. "Development of a smart workstation for use in mammography", in Proceedings of SPIE, vol. 1445 (1991), pp. 101 103; 4 pages.
Giger et al., "An Intelligent Workstation for Computer-aided Diagnosis", in RadioGraphics, May 1993, 13:3 pp. 647 656; 10 pages.

Non final office action dated Jan. 22, 2016 for U.S. Appl. No. 14/360,389.
"Predicting tumour location by simulating large deformations of the breast using a 3D finite element model and nonlinear elasticity" by P. Pathmanathan et al., Medical Image Computing and Computer-Assisted Intervention, pp. 217-224, vol. 3217 (2004).
"ImageParser: a tool for finite element generation from three-dimensional medical images" by H. M. Yin et al., BioMedical Engineering OnLine. 3:31, pp. 1-9, Oct. 1, 2004.
"Biomechanical 3-D Finite Element Modeling of the Human Breast Using MRI Data" by A. Samani et al. IEEE Transactions on Medical Imaing, vol. 20, No. 4, pp. 271-279. 2001.
"Mammogram synthesis using a 3D simulation. I. breast tissue model and image acquisition simulation" by Bakic et al., Medical Physics. 29, pp. 2131-2139 (2002).
Non Final Office action dated Nov. 20, 2015 for U.S. Appl. No. 14/549,604.
Response to Non Final Office action dated May 23, 2016 for U.S. Appl. No. 14/360,389.
Final Office Action dated Jul. 5, 2016 for U.S. Appl. No. 14/360,389.
Response to Final Office Action dated Aug. 15, 2016 for U.S. Appl. No. 14/360,389.
Advisory Action dated Aug. 24, 2016 for U.S. Appl. No. 14/360,389.
Pre-Appeal Brief Request for Review dated Oct. 4, 2016 for U.S. Appl. No. 14/360,389.
Appeal Brief dated Dec. 4, 2016 for U.S. Appl. No. 14/360,389.
Examiner's Answer to Appeal Brief dated Jan. 31, 2017 for U.S. Appl. No. 14/360,389.
Reply Brief dated Mar. 6, 2017 for U.S. Appl. No. 14/360,389.
Decision on Appeal dated Nov. 8, 2017 for U.S. Appl. No. 14/360,389.
Non-Final Office Action dated Mar. 9, 2017 for U.S. Appl. No. 15/088,844.
Notice of Allowance for U.S. Appl. No. 15/088,844 dated Jun. 29, 2017.
Notice of Allowance for U.S. Appl. No. 15/088,844 dated Mar. 28, 2017.
Office Action dated Mar. 10, 2017 for Canadian Application No. 2,702,782, Owner Hologic, Inc., based on PCT/US2009/065288, 3 pages.
Office Action dated Jan. 11, 2017 for Japanese Patent Application No. 2014-556824, Applicant Hologic, Inc., including English Translation provided by Japanese associate, 12 pages.
Computer generated translation of Foreign Patent Reference JP 2003-189179 A, published Jul. 4, 2003,16 pages.
International Preliminary Report on Patentability for International Publication No. PCT/US2009/065288 dated Feb. 18, 2014.
Notice of Allowance dated Jan. 22, 2018 for U.S. Appl. No. 14/360,389.
Office action dated Feb. 1, 2018 for U.S. Appl. No. 15/802,225.
Office Action dated Feb. 19, 2018 for EP Application 12851085.6, Applicant Hologic, Inc. 5 pp.
Extended EP Search Report for EP Application No. 17176956.5 dated Apr. 3, 2018, 7 pages.
Notice of Allowance dated May 21, 2018 for U.S. Appl. No. 14/360,389.

* cited by examiner

SYSTEM AND METHOD FOR GENERATING A 2D IMAGE USING MAMMOGRAPHY AND/OR TOMOSYNTHESIS IMAGE DATA

RELATED APPLICATIONS

This application is a continuation of U.S. patent application Ser. No. 14/360,389, filed May 23, 2014, which is a National Phase entry under 35 U.S.C. § 371 of International Patent Application No. PCT/US2012/66526, having an international filing date of Nov. 26, 2012, which claims priority under 35 U.S.C. § 119 to U.S. Provisional Patent Application No. 61/563,785, filed Nov. 27, 2011. This application is also related to U.S. patent application Ser. No. 12/471,981, filed May 26, 2009, now U.S. Pat. No. 8,571,289; U.S. patent application Ser. No. 12/276,006, filed Nov. 21, 2008, now U.S. Pat. No. 7,760,924; U.S. application Ser. No. 11/827,909, filed Jul. 13, 2007, now U.S. Pat. No. 7,616,801; U.S. patent application Ser. No. 11/604,069, filed on Nov. 24, 2006, now abandoned; and U.S. application Ser. No. 11/271,050, filed Nov. 11, 2005, now U.S. Pat. No. 7,577,282. Each of the above applications is hereby incorporated by reference.

FIELD

This patent specification pertains to x-ray mammography and tomosynthesis, and more specifically to techniques and equipment for acquiring and/or synthesizing, processing, storing and displaying mammograms, tomosynthesis projection images, synthesized two-dimensional (2D) images and/or tomosynthesis reconstructed images, and to medical image softcopy reading systems, to hanging protocols and to other medical image display features.

BACKGROUND

Mammography has long been used to screen for breast cancer and other abnormalities and for diagnostics. Traditionally, mammograms were formed on X-ray film, but more recently flat panel digital imagers have been introduced that acquire a mammogram in digital form and thereby facilitate analysis and storage and provide other benefits as well. Further, substantial attention and technological development has been dedicated towards obtaining a three-dimensional image of the breast, using methods such as breast tomosynthesis. In contrast to the 2D images generated by legacy mammography systems, breast tomosynthesis systems construct a 3D image volume from a series of 2D projection images, each projection image obtained at a different angular displacement of the x-ray source relative to the image detector as the x-ray source is scanned over the detector. The constructed 3D image volume is typically presented as a plurality of slabs or slices of image data, the slabs geometrically reconstructed on planes parallel to the imaging detector. The reconstructed tomosynthesis slices reduce or eliminate the problems caused by tissue overlap and structure noise in single slice two-dimensional mammography imaging by permitting a radiologist to scroll through the slabs and view underlying structures.

Tomosynthesis systems have recently approved for breast cancer screening and diagnosis. The assignee of this patent specification, Hologic, Inc., has demonstrated at trade shows in this country a fused, multimode mammography/tomosynthesis system that takes either or both types of mammogram and tomosynthesis images, either while the breast remains immobilized or in different compressions of the breast. Other companies have proposed the introduction of systems which are dedicated to tomosynthesis imaging, i.e., which do not include the ability to also acquire a mammogram.

Restricting systems to tomosynthesis acquisition and image display may present an obstacle to acceptance of the tomosynthesis imaging technology, as medical professionals have grown accustomed to screening and analysis of mammogram images. Mammograms offer good visualization of micro-calcifications, and can offer higher spatial resolution when compared with tomosynthesis images. While tomosynthesis images provided by dedicated breast tomosynthesis systems in the art have other desirable characteristics (i.e., better visualization of structures), such systems do not leverage the existing interpretation expertise of medical professionals.

One method of leveraging existing medical expertise to facilitate the transition to tomosynthesis technology was described in U.S. Pat. No. 7,760,924, entitled "System and Method for Generating a 2D Image from a Tomosynthesis Data Set." The '924 patent describes a method of generating a synthesized 2D image which may be displayed along with tomosynthesis projection or reconstructed images, to assist in screening and diagnosis.

SUMMARY

According to one aspect of the invention, it is realized that an improved synthesized 2D image may be obtained by merging the most relevant data from a plurality of data sources. In one embodiment, the merging is performed using a combination of 2D and 3D image data, wherein the 2D image may include either an acquired mammogram, a synthesized mammogram, or a tomosynthesis projection image, and the 3D image data may comprises a reconstructed 3D data set. In an alternate embodiment, the merged data is formed using 3D projection images and/or reconstruction images. The improved synthesized image, referred to herein as a 'merged' image $I_{MERGE}$, incorporates the most relevant information from all acquired and computer generated data sets into one 'supreme' 2D image for display on a workstation. Thus, regions of pixels in the displayed merged image may be sourced by different images in a data set including but not limited to one or more of an acquired 2D image (mammogram or tomosynthesis projection image), a synthesized 2D image, or a reconstructed tomosynthesis slice or slab. The particular regions may be identified statically (i.e., within a particular grid), or dynamically, and may range in granularity from one pixel to all pixels in the image. With such an arrangement, the radiologist may quickly view a large number of regions of interest within a breast while referencing only a single 2D image, thereby increasing the performance and efficiency of breast cancer screening and diagnosis.

According to a further aspect of the invention, a map is automatically generated for each region in the merged image, identifying the particular image that sourced the region in the merged image. An interface feature may be provided that enables the origin source image to be displayed when the region is selected by the user. The origin source image may be displayed in a variety of manners, e.g., overlaid over the merged image to allow toggling between the two images or display using cine mode, or displayed adjacent to the merged image, etc.

According to a further aspect of the invention, it is determined that particular types of images may include different types of relevant information. For example, calcifications are best visualized in 2D mammograms, while masses are best visualized using 3D reconstructed images. In one embodiment, different filters are applied to each of the different types of images (i.e., 2D and 3D), where the filters are selected to highlight the particular characteristics of the images which are best displayed in the respective imaging mode. Appropriate filtering of the respective types of images prior to the merge ensures that the final merged image includes the most relevant information that can be obtained from all image types. Alternatively, the type of filtering that is performed for the various images may be defined via user input, which permits a user to select a 'merge mode', for example, geared towards highlighting masses, calcifications, or making the merged image appear to be a particular image type, such as a 3D reconstructed slice, or a 2D mammogram.

Merging of the images may be done in a variety of ways. According to one embodiment, general purpose Computer Assisted Diagnosis (CAD) algorithms are used to identify features within each of the 2D and 3D images. The various features are assigned weights, and the merged image is built by selecting the image having the region with the most significant weight. The size of the region may vary in granularity from one pixel to many (or even all) pixels, and may be statically pre-defined, or may have margins which vary in accordance with the varying thresholds of the source images.

In accordance with a further aspect of the invention, it is envisioned that the merged image may be pre-processed and stored following tomosynthesis acquisition, or dynamically generated in response to a request for a merged image at a radiologist work station.

It is realized that the visualization of such a merged image may have some drawbacks. For example, there may be neighboring regions in the merged image which exhibit bright calcifications but in fact are sourced from image slices which are distant from one another in the z-plane. Therefore, what may appear to as a mass of calcifications in the merged image may, in fact, be calcifications which are distributed throughout the breast and thus do not actually represent a calc cluster that requires further review. According to a further aspect of the invention, this problem is overcome by the inclusion of a cluster spread indicator. The cluster spread indicator is a graphical indicator provided with the merged image, and visually indicates the distribution of calcifications along the z-plane, allowing the medical professional to quickly assess whether a group of calcifications comprise a calcification cluster.

One aspect of the invention includes a method including the steps of obtaining a plurality of images, each of the images in the plurality having at least one corresponding region, generating a merged image, the merged image also having the corresponding region, the step of generating including: selecting an image source from the plurality of images to source image data for the corresponding region in the merged image by comparing attributes of the corresponding regions of the plurality of images to identify the image source having preferred attributes.

The foregoing aspect can include any one or more of the following embodiments. The preferred attributes includes attributes indicative of regions of interest, such as cancers, or alternatively such as more accurate representation of breast density or breast anatomy (e.g. truthful breast-border/nipple appearance). In general, any attribute capable of delivering a high/better-quality image can be relevant here. The method can further include filtering the plurality of images to magnify attributes of the plurality of images. The filtering can apply different filters to images of different types. The method can further include visually indicating a distribution of the preferred attributes in the corresponding region by providing a histogram to illustrate a depth of the preferred attributes. The plurality of images can comprise a 2D image and a 3D image. The plurality of images can be selected from a group consisting of tomosynthesis projection images, reconstructed tomosynthesis slices, mammograms, and synthesized two dimensional images. The method can further include generating a map for a region in the merged image, whereby the map identifies at least one of the plurality of images that sourced the region in the merged image. The method can further include displaying the at least one of the plurality of images that sourced the region when the region is selected by a user. The at least one of the plurality of images that sourced the region can overlay the merged image such that a user can view both types of images at the same time or by toggling between the types.

According to another aspect of the invention, a display workstation comprises an interface, the interface including a mechanism which, upon selection, results in the generation and/or display of a merged image, the merged image comprising a two dimensional synthesized image comprising a plurality of regions, wherein at least two of the regions are sourced by different images selected from a group of images, and wherein the group of images include tomosynthesis projection images, tomosynthesis reconstruction slices, mammograms and synthesized 2D images.

The foregoing aspect can include any one or more of the following embodiments. The interface can further include a mode selection mechanism enabling a user to select a mode of either generation or display of the merged image. The interface can further include a mechanism for selecting a region of the merged image and a mechanism for displaying three-dimensional information related to the selected region on a display station. Additionally or alternatively, the generation of the merged display does not take place at the workstation, but can happen in another part of the system. The interface can display a map for at least one of the plurality of regions in the merged image such that a user can select at least one of the plurality of regions to display one of the group of images that sourced the at least one of the plurality of regions. The interface can allow a user to view both of or toggle between the merged image and the one of the group of images that sourced the at least one of the plurality of regions. The interface can provide a graphical indicator along with a display of the merged image such that the graphical indicator illustrates a depth of attributes within the regions. The interface can display simultaneously, sequentially, or in toggle mode two or more of the merged image, the tomosynthesis projection image, the tomosynthesis reconstruction slice, the mammogram and the synthesized 2D image.

The present invention can include any one or more of the foregoing aspects and/or embodiments, in any combination, and can include any one or more of any of the details described herein.

These and other aspects of the invention will be described in more detail with regard to the below figures.

DETAILED DESCRIPTION OF PREFERRED EMBODIMENTS

Figure 1:
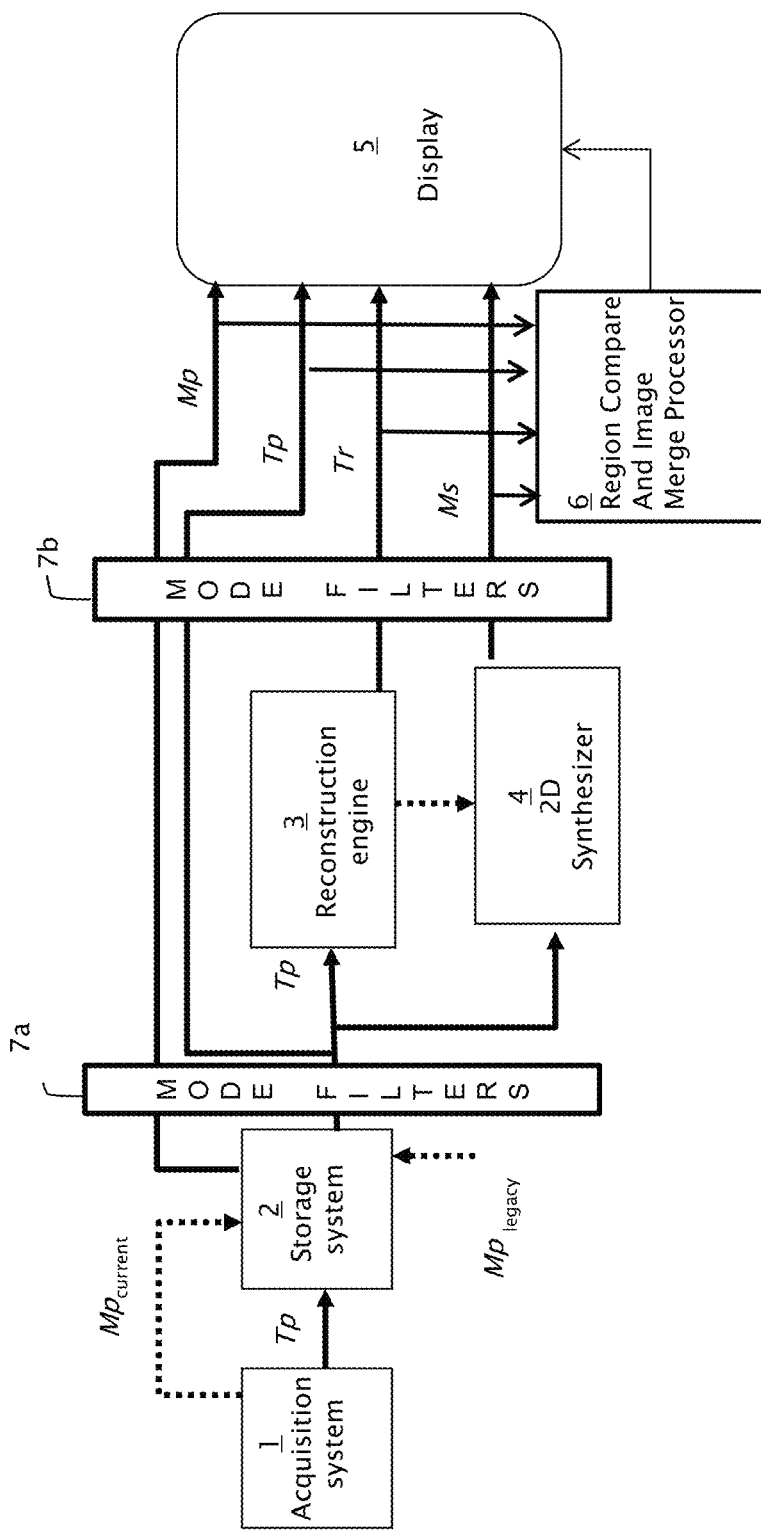
FIG. 1 is a block diagram illustrating flow of data through a system which includes a combination mammography/tomosynthesis acquisition station or a tomosynthesis only acquisition station to acquire tomosynthesis and/or mammography images, and includes image merge technology of the present invention for providing a supreme synthesized two dimensional image which merges the most relevant data from all available data sources into one 2D image.

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

The following abbreviations shall have the following definitions throughout this application. The notation Mp refers to a conventional mammogram, which is a two-dimensional projection image of a breast and encompasses both a digital image as acquired by a flat panel detector or another imaging device and the image after conventional processing to prepare it for display to a health professional or for storage, e.g. in the PACS system of a hospital or another institution.

Tp refers to an image that is similarly two-dimensional but is taken at a respective tomosynthesis angle between the breast and the origin of the imaging X-rays (typically the focal spot of an X-ray tube), and also encompasses the image as acquired as well as the image after being processed for display or for some other use. Tr refers to an image that is reconstructed from images Tp, for example in the manner described in said earlier-filed patent applications, and represents a slice of the breast as it would appear in a projection X-ray image of that slice at any desired angle, not only at an angle used for Tp or Mp images.

The term Ms refers to synthesized 2D projection images which simulate mammography images, such as a craniocaudal (CC) or mediolateral oblique (MLO) images, and are constructed using tomosynthesis projection images Tp, tomosynthesis reconstructed images Tr or a combination thereof. Ms images may be provided for display to a health professional or for storage in the PACS system of a hospital or another institution. An example of methods that may be used to generate synthesized 2D projection images are described in U.S. patent application Ser. No. 12/471,981, filed May 26, 2009, as well as U.S. Pat. No. 7,760,924, filed Nov. 21, 2008, both incorporated herein by reference in their entireties.

The term $I_{MERGE}$ refers to a 2D image generated by merging together any two or more of Mp, Ms, Tp or Tr images.

The terms $I_{MERGE}$, Tp, Tr, Ms and Mp also encompasses information, in whatever form, that is sufficient to describe such an image for display, further processing, or storage. The images $I_{MERGE}$, Mp, Ms, Tp and Tr typically are in digital form before being displayed, and are defined by information identifying properties of each pixel in a two-dimensional array of pixels. The pixel values typically relate to respective measured or estimated or computed responses to X-rays of corresponding volumes in the breast (voxels or columns of tissue). In a preferred embodiment, the geometry of the tomosynthesis images (Tr and Tp), mammography images (Ms, Mp) and the merged image $I_{MERGE}$ are matched to a common coordinate system as described in U.S. patent application Ser. No. 11/667,650 "Matching Geometry Generation and Display of Mammograms and Tomosynthesis Images", filed Nov. 15, 2005 and incorporated herein by reference.

FIG. 1 illustrates flow of data in one example of an image generation and display system which may incorporate the merged image generation and display features of the present invention. It should be understood that FIG. 1 illustrates a particular embodiment of a flow diagram, with certain processes happening in a particular serial order or in parallel, the present invention is not generally limited to the performance of image processing in any particular order.

FIG. 1 illustrates an image data acquisition system 1 that acquires tomosynthesis image data for Tp images of patients' breasts using the three dimensional and/or tomosynthesis acquisition methods of any of the systems available in the art. If the acquisition system is a combo system, Mp images may also be generated. Some dedicated tomosynthesis systems or combo systems may be adapted to accept and store legacy mammogram images (meaning pre-acquired mammogram systems indicated via dashed line and legend $Mp_{legacy}$ in FIG. 1) in a Picture Archiving and Communication System (PACS) storage device 2, although it is not a requirement that any Mp images be acquired by the acquisition system or pre-stored.

Following tomosynthesis image acquisition, the projection images Tp are sent to storage device 2, which is preferably a DICOM-compliant PACS. When images are needed for display 5, the Tp images are sent (from either acquisition system 1 or from storage device 2) to a computer system 3 configured as a reconstruction engine that reconstructs the Tp images into reconstructed image slabs Tr representing breast slices of selected thickness and at selected orientations, as disclosed in said earlier-filed patent applications and detailed below. The computer system may be further configured with 2D synthesis functionality 4, which may operate substantially in parallel with reconstruction engine 3 to generate a synthesized 2D image (interchangeably referenced as T2d or Ms). The reconstructed slice images Tr are then sent to a display system 5 so that they can be viewed. Additionally or alternatively the Tr slices can be returned to the storage device. If the reconstruction engine 3 is connected to display 5 via a fast link, then large datasets can be transmitted quickly. Other images, such as the Ms, Mp and/or Tp images may also be forwarded to the display unit for concurrent or toggled viewing.

As shown in FIG. 1, the imaging and display system of the present invention includes a 2D synthesizer for generating 2D images simulating mammograms taken at both a CC and MLO orientation using a combination of one or more Tp and/or Tr images. The synthesized 2D images may be generated dynamically prior to display, as shown in FIG. 1, and/or may be stored in storage system 2 for use by other processes.

As will be described in more detail later herein, a set of mode filters 7a, 7b are disposed between image acquisition and image display. Each of the filters 7a and 7b may additionally include customized filters for each type of image (i.e., Tp, Mp, Tr) arranged to highlight certain aspects of the particular types of images. Thus each mode can be tuned/configured in a optimal way for a specific purpose. The tuning or configuration may be automatic, based on the type of the image, or may be defined by manual input, for example through a user interface coupled to a display. For example, filters could be provided to define a mass/calc-emphasis mode, 3D-tomo-slice-look mode, 2D-mammo-look mode, etc.

According to one aspect of the invention, an image merge processor 6 merges relevant image data obtained from a set of available images to provide a merged image $I_{MERGE}$ for display. The set of available images includes at least filtered and/or unfiltered Ms, Mp, Tr and/or Tp images. It should be noted that although FIG. 1 illustrates that all types of images are input into the image merge processor 6 it is envisioned that the form of merged image shall be manually configurable. Thus a user interface, comprised of a keypad, touch pad, mouse, pull down menu, button, switch, etc., may be configured to allow a user to select a particular group of two or more images or image types for merging to produce a supreme 2D image for display. For example, a radiologist may wish to merge two or more reconstructed tomosynthesis slabs to provide a merged image showing the most discernable structures in a single image. Alternatively, the radiologist may combine the 2D mammogram image, Mp or Ms, with 3D projection or reconstructed images to obtain a merged image that highlights both calcifications and structures. Filters applied to each type of image further highlight the types of structures or features which are generally most prevalent or discernable in the image type; thus a certain filter may be applied to mammography images to highlight calcifications, while a different filter may be applied to tomosynthesis slices to highlight masses. Filters may also be provided to give the particular image a desired look and feel; i.e., make the merged image appear more like a tomosynthesis image, or a mammography image.

The display 5 may be the display of an acquisition workstation, or a technologists review station, or a display that is physically remote from the acquisition system or storage device, i.e., connected via the network.

A display of the system preferably should be able to display $I_{MERGE}$, Ms, Mp and Tr (and/or Tp) images concurrently (either in separate windows on the display, on separate monitors of a technology workstation, or overlaid) or sequentially or in toggled mode, wherein the $I_{MERGE}$ Ms, Mp, Tp and Tr images may be those currently acquired, or those that were acquired in previous studies. Thus, in general, the display can simultaneously or sequentially or in toggled mode display merged images $I_{MERGE}$, mammograms (Ms, Mp) and tomosynthesis images Tr (and/or Tp) from the current and previous studies. Tr slices can be reconstructed all to the same size, which can be the same as the size of an Mp or Ms image of the breast, or they can be initially reconstructed to sizes determined by the fan shape of the x-ray beam used in the acquisition and later converted to that same size by appropriate interpolate]on/extrapolation.

Images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image that is concurrently displayed or with which the displayed image is or can be toggled. For example, if two images of the same breast are taken and are not the same size or do not have the same special resolution, provisions are made to selectively zoom in or zoom out one of them, or zoom both, such that they appear to be the same size on the screen when they are concurrently displayed or the user toggles between them, to facilitate comparison or to otherwise facilitate detection/diagnosis. Known interpolation/extrapolation and weighting techniques can be used in such re-sizing, and known image processing technology can be used to make other characteristics of the displayed images similar in a way that facilitates detection/diagnosis. When viewing such resized images, according to one aspect of the invention the merged image $I_{MERGE}$ is automatically resized accordingly.

The system described as a non-limiting example in this patent specification is thus capable of receiving and displaying selectively the tomosynthesis projection images Tp, the tomosynthesis reconstruction images Tr, the synthesized mammogram image Ms and/or the mammogram images Mp, or a single type, or any sub combination of types. The system has software to perform reconstruction of tomosynthesis image data for images Tp into images Tr, software for synthesizing mammogram images Ms and software for merging a set of images to provide a supreme image that displays, for every region of the merged image, the most relevant feature in that region among all images in the image set.

For the purpose of this application, a feature is the 'most relevant' based upon the application of one or more a computer assisted detection (CAD) algorithms to the image, wherein the CAD algorithms assign numerical values, weights or thresholds, to pixels or regions based upon detected features within the region or between features. The features may include, for example, speculated lesions, calcifications and the like. Various systems and methods are currently known for computerized detection of abnormalities in radiographic images, such as those disclosed by Giger et al. in RadioGraphics, May 1993, pp. 647 656; Giger et al. in Proceedings of SPIE, Vol. 1445 (1991), pp. 101 103; U.S. Pat. No. 4,907,156 to Doi et al.; U.S. Pat. No. 5,133,020 to Giger et al.; U.S. Pat. No. 5,343,390 to Doi et al.; U.S. Pat. No. 5,491,627 to Zhang et al.

Figure 2:
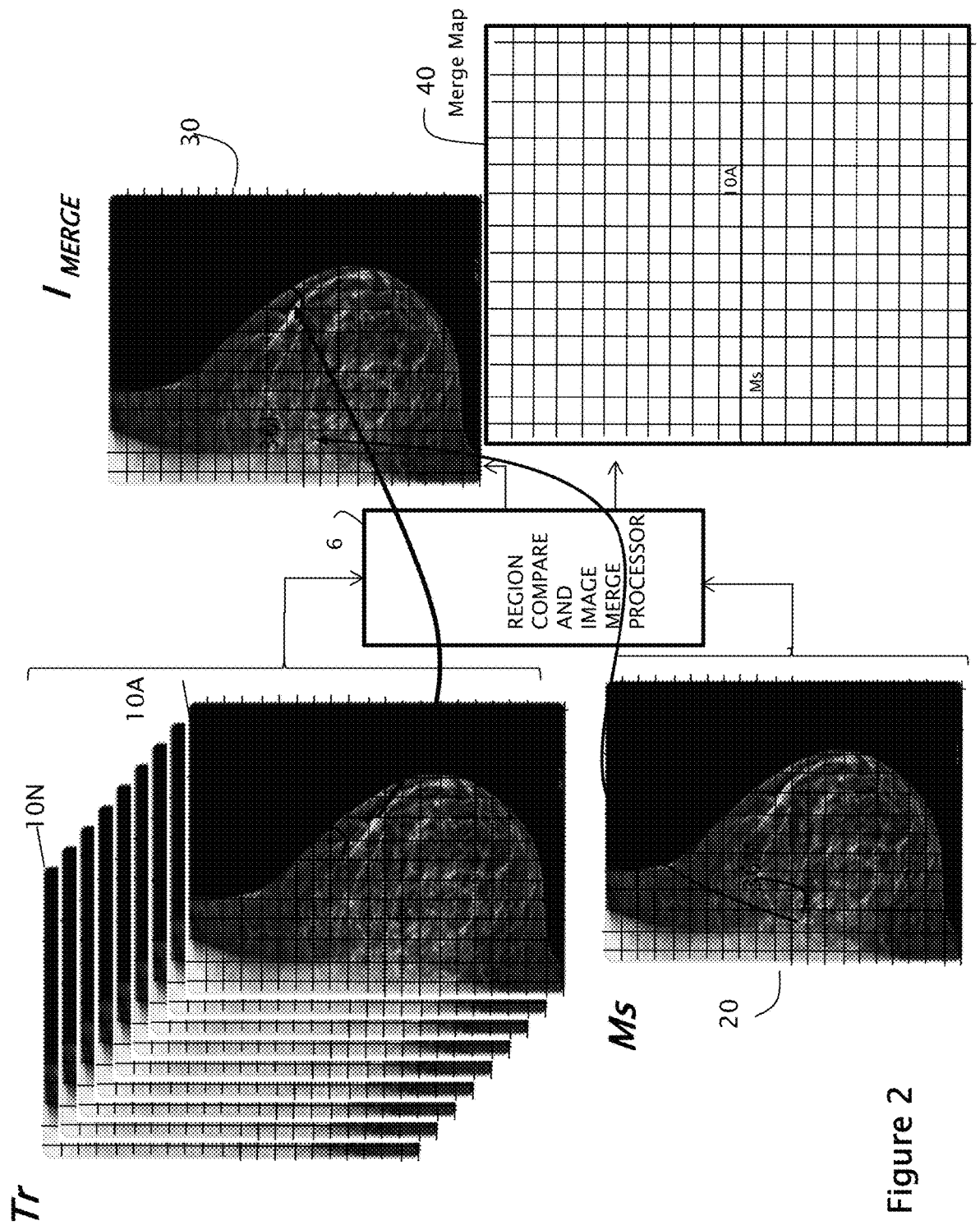
FIG. 2 is diagram illustrating the data flow of a series of tomosynthesis slices, a synthesized 2D mammogram through the image merge technology of the present invention to generate at least one of a merged image $I_{MERGE}$ and a merge map.

FIG. 2 is a diagram which pictorially illustrates the merging of image data from a tomosynthesis image data set Tr, comprising tomosynthesis slices 10A to 10N, with image data from a mammogram 20, in this case a synthesized mammogram Ms. For ease of description filters are not shown in this example. The image data is forwarded to the region compare and image merge processor 6 which compares the images on a region by region basis, searching for that image with the most desirable display data for that region. The image with the most desirable display data may be that image with a highest pixel value, the lowest pixel value, or which has been assigned a threshold value or weight based on the application of a CAD algorithm to the image. When the image with the most desirable display data for that region is identified, the pixels of that region are copied over to the corresponding region of the merged image. For example, as shown in FIG. 2, region 36M from image Ms is written to region 361 of the merged image, and region 35Tr of tomosynthesis slice 10A is copied to region 351 of the merged image.

As the regions of the merged image are populated, a merge map 40 is constructed. The merge map stores, for each region of the merged image, an identifier of the image which sourced the region. Therefore, as shown in FIG. 2, the Ms identifier is stored in region 361, while the 10A TR slice identifier is stored in region 351. As will be described in more detail later herein, the merged map may be used during merge image display to permit fast viewing of the source image for a selected region.

Figure 3:
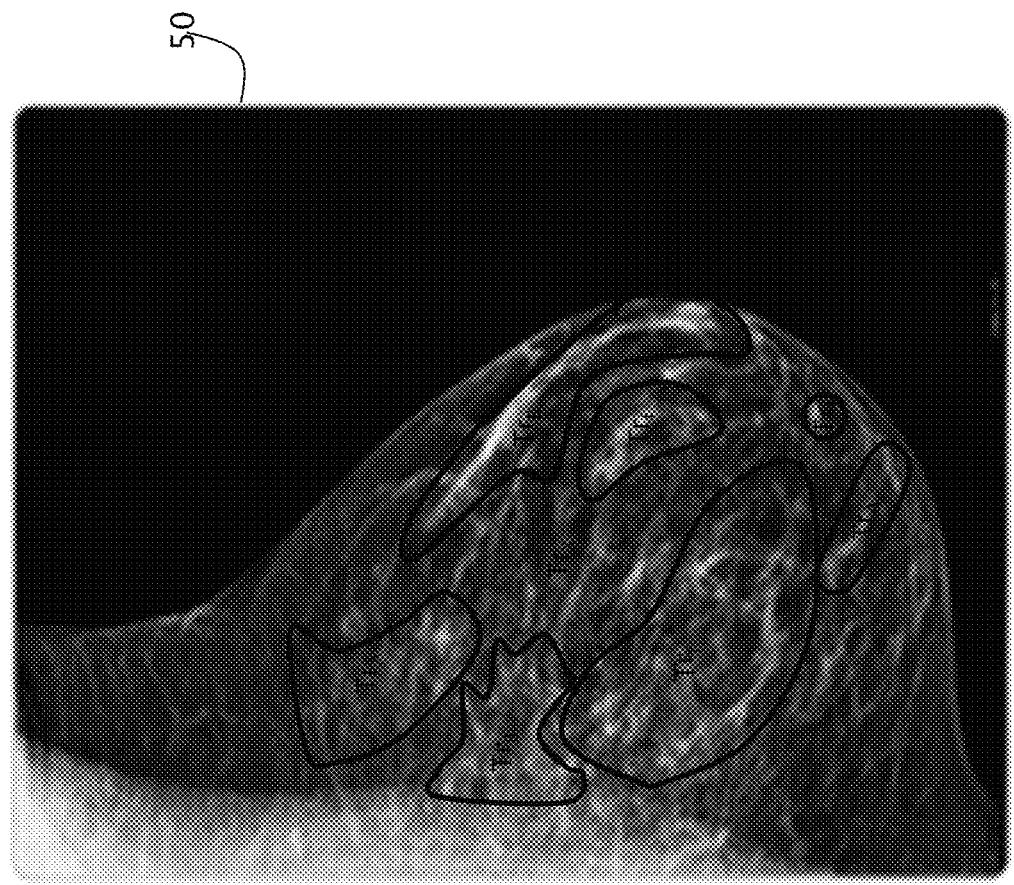
FIG. 3 is a diagram illustrating an alternate form of merged image, wherein region boundaries are dynamically identified during merge image build.

Although the regions of FIG. 2 have been shown as pre-defined grid regions it is not necessary that regions be pre-defined in this manner. Rather, according to one aspect of the invention, the boundaries of the regions are dynamically identified during the region compare and image generation process by performing comparisons at pixel or multi-pixel granularities. FIG. 3 illustrates a merged image 50 which has been constructed via the combinations of numerous regions of different source images, at arbitrary region boundaries 52. For example, as shown in FIG. 3, the boundaries 52 may be identified according to the detection of particular features within the slices.

Figure 4:
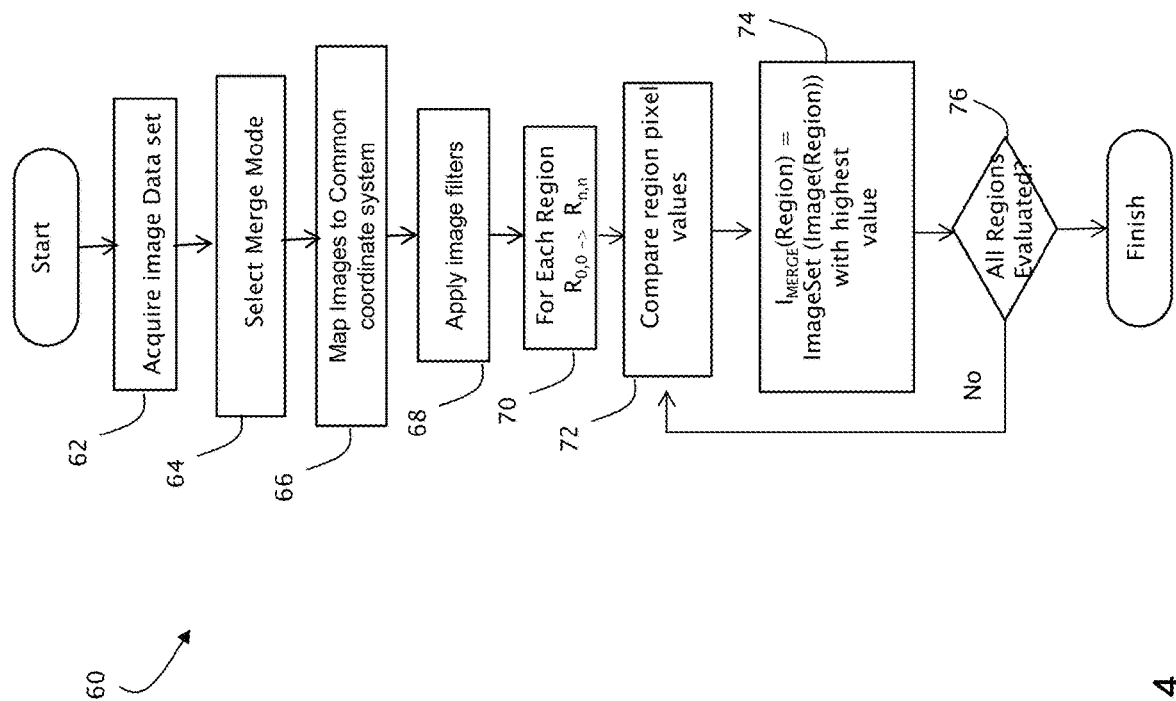
FIG. 4 is flow diagram illustrating exemplary steps that may be performed during an image merge process of the present invention.

FIG. 4 is a flow diagram provided to illustrate exemplary steps that may be performed in an image merge process of the present invention. At step 62 an image data set is acquired. The image data set may be acquired by a tomosynthesis acquisition system, a combo tomosynthesis/mammography system, or acquired merely by retrieving pre-existing data from a storage device, either locally or remotely located relative to an image display device. At step 64 a user may optionally select a merge mode. As part of selecting a merge mode, the user may select which images to use for the merge, whether to highlight certain features, such as calcifications, speculated lesions or masses, whether to display the image as a lower resolution tomosynthesis image, etc. At step 66 the images that are to be merged to build the supreme view are mapped to a common coordinate system, for example as described in U.S. Pat. No. 7,702,142 entitled *Matching Geometry Generation and Display of Tomosynthesis Images*, incorporated herein by reference. Other methods of matching images of different coordinate systems may alternatively be used.

At step 68, image filters are applied and, for each of the regions (indicated by "step" 70), the process of comparing regions among the different images begins, indicated by step 72. At step 74, each $I_{MERGE}$ region is populated with the pixels of the region of the image in the image set having the most desirable pixels, value or pattern. The process of populating regions continues until it is determined, at step 76, that all regions have been evaluated, at which point the merged image is ready for display.

Figure 5A:
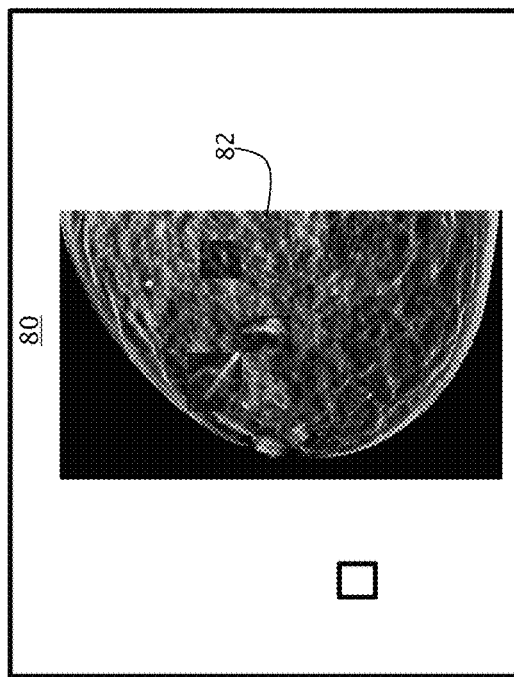
FIGS. 5A and 5B illustrate a display of a merged image, and a resultant display of a source image when a region is selected by a user.
Figure 5B:
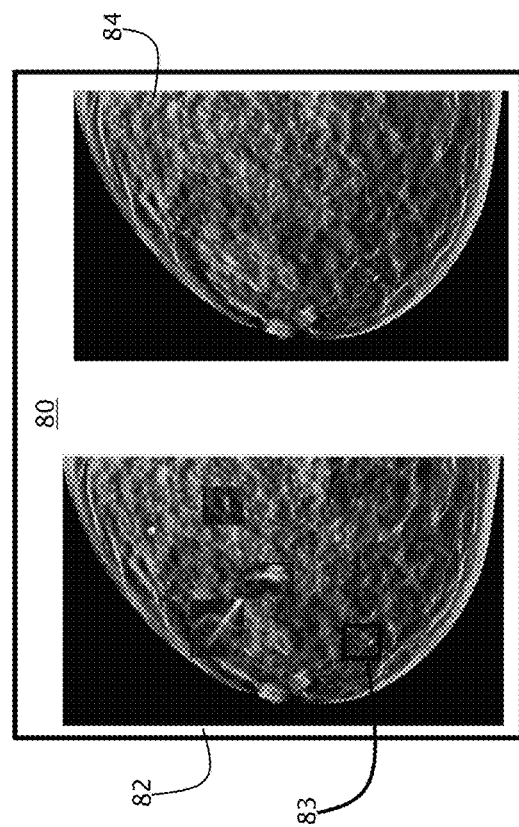

FIGS. 5A and 5B illustrate two views of a display 80. The first view of display 80 shown in FIG. 5A illustrates a merged image 82, having regions sourced by different ones of an acquired or synthesized image set. FIG. 5B illustrates one feature enabled by the present invention, whereby a user may select a region or area 83 within the merged image 82, and the resulting image source 84 for that area is displayed together with the merged image. Of course the image need not be displayed proximate to the merged image; in one embodiment, selection of a desired region replaces the merged image with the source image, or alternatively overlays the source image on the merged image, allowing the two to be viewed in cine mode or toggle mode. Multiple source images may be displayed concurrently in this manner, i.e., when a user selects multiple regions within the merged image a 'stack', pull down menu or other means is used for concurrent display of the multiple images. The merged image may automatically be shrunk to an icon, or moved to a task bar.

The merged image may also be dynamically modified by the selection of different filters, modes or sources at a user interface of the display.

Figure 6:
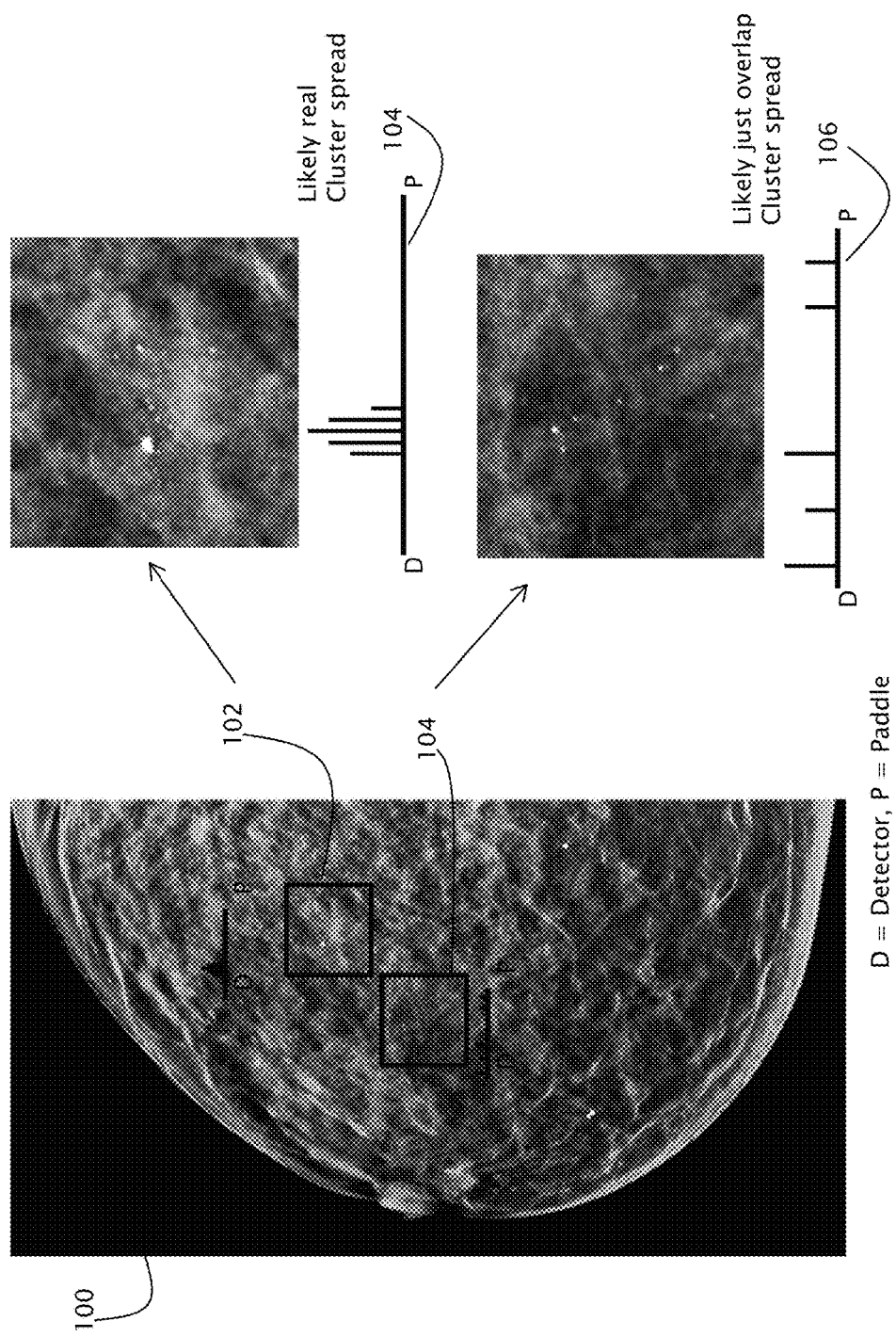
FIG. 6 is a diagram of an exemplary merged image display, which incorporates an optional cluster spread indicator of the present invention.

According to another aspect of the invention, it is realized that a merged image may obfuscate data presented to the reviewer by essentially removing depth information provided by the tomosynthesis reconstruction. For example, as shown in FIG. 6, merged image 100 appears to include multiple clusters of calcifications 102*a* and 102*b*, which are potential predictors of cancer. However, in a merged image, the respective clusters of calcifications 102*a* and 102*b*, which appear proximate when evaluating only in the x-y axis, may actually be spread apart throughout the breast. To reduce the chance of a false positive cancer indication, the present invention includes a histogram 104, 106, which pictorially illustrates the depth of the clusters of calcifications 102*a* and 102*b* within the respective magnified regions. Histogram 104 illustrates that the cluster of calcifications 102*a* are actually a real calcification cluster, while Histogram 106 illustrates that the visualized cluster of calcifications 102*b* are actually distributed throughout the breast.

Figure 7:
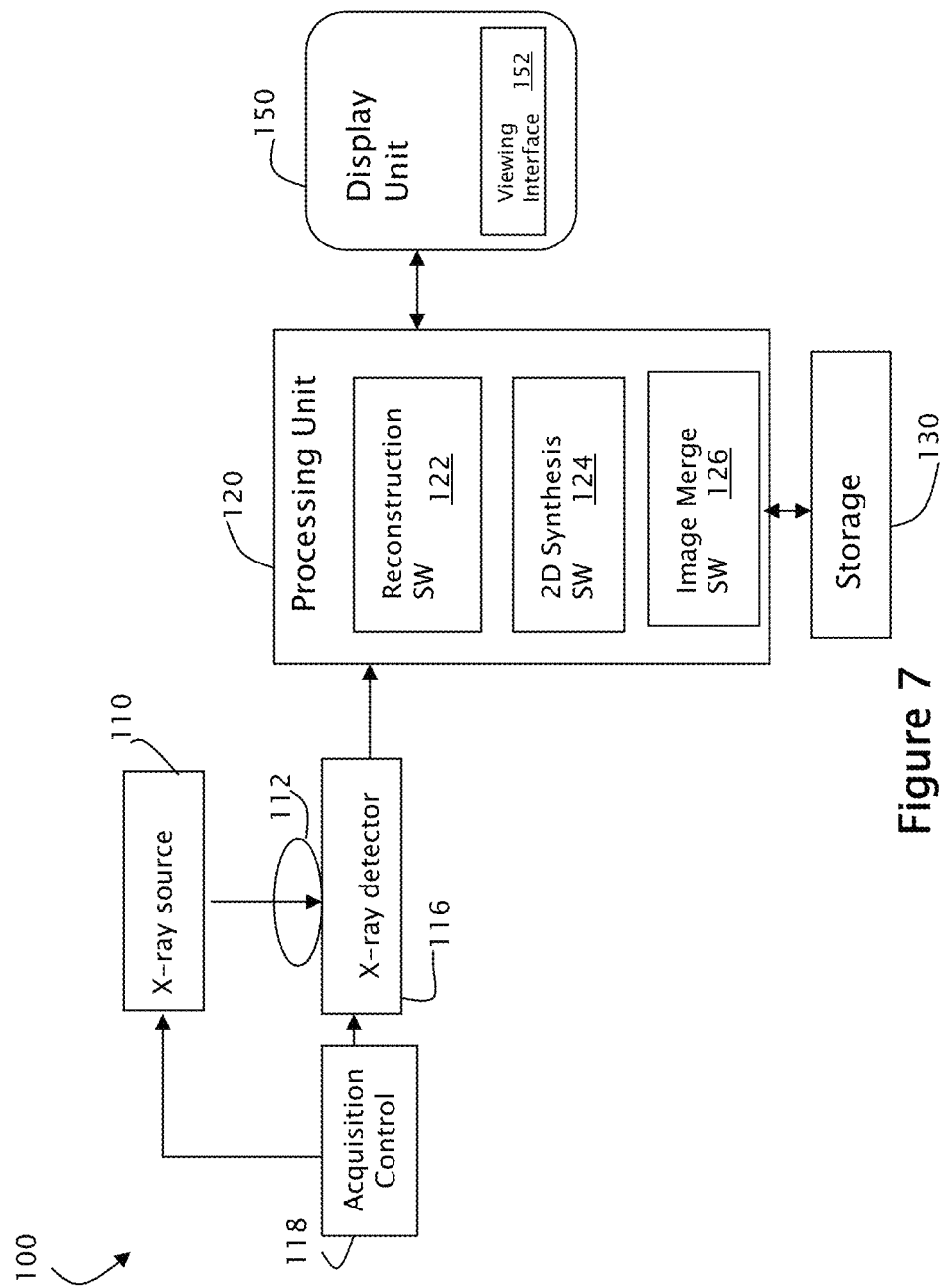
FIG. 7 is an x-ray image acquisition, processing and display system.

FIG. 7 is schematic illustration of an x-ray image acquisition, processing and display system 108. The system 108 includes an x-ray source 110 that projects x-rays 112 at a detector 116 in order to acquire x-ray images of breast tissue under the control of an acquisition control 118. The acquired images are transmitted to a processing unit 120, which generates a reconstructed 3D image set 122, a 2D synthesized image 124, and a synthesized merged image 126, as described herein. These constructed/generated images may be stored in a storage memory 130 coupled to the processor 120 and/or displayed on a viewing interface 152 of a display unit 150.

Accordingly, a system and method for merging the most relevant data from a plurality of data sources to provide a 'merged' image $I_{MERGE}$ for display has been shown and described. The merged image may combine regions of any combination of 2D and 3D image data, including an acquired mammogram, a synthesized mammogram, or a tomosynthesis projection image and a reconstructed 3D data set, thereby allowing the radiologist to quickly view a large number of regions of interest within a breast while referencing only a single 2D image and increasing the performance and efficiency of breast cancer screening and diagnosis.

Having described exemplary embodiments, it can be appreciated that the examples described above are only illustrative and that other examples also are encompassed within the scope of the appended claims. For example, flow diagrams are illustrative of exemplary steps; the overall image merge may be achieved in a variety of manners using data merge methods known in the art. The system block diagrams are similarly representative only, illustrating functional delineations that are not to be viewed as limiting requirements of the invention. Thus the above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A method, comprising:
    obtaining a plurality of images, each of the images in the plurality having at least one corresponding region;
    generating a synthesized 2D mammography image, the synthesized 2D mammography image also having the corresponding region, wherein the synthesized 2D mammography image is generated by
    selecting an image source from the plurality of images to source image data for the at least one corresponding region in the synthesized 2D mammography image by comparing attributes of the at least one corresponding region in one or more of the plurality of images to identify the image source having preferred attributes;
    generating a map for the synthesized 2D mammography image, whereby the map identifies at least one of the plurality of images that sourced the corresponding region in the synthesized 2D mammography image; and
    displaying at least one of the synthesized 2D mammography image and the source image data for the at least one corresponding region.

2. The method of claim 1, wherein the preferred attributes include attributes indicative of potential cancers.

3. The method of claim 1 further comprising filtering the plurality of images to magnify attributes of the plurality of images.

4. The method of claim 3, wherein filtering applies different filters to images of different types.

5. The method of claim 1 further comprising visually indicating a distribution of the preferred attributes in the corresponding region by providing a histogram to illustrate a depth of the preferred attributes.

6. The method of claim 1, wherein the plurality of images include 3D projection or reconstruction images.

7. The method of claim 1, wherein the plurality of images is selected from a group consisting of tomosynthesis projection images, reconstructed tomosynthesis slices, mammograms, and synthesized two dimensional images.

8. The method of claim 1, wherein the at least one of the plurality of images that sourced the at least one region overlays the synthesized 2D mammography image such that a user can view both types of images at the same time or by toggling between the types.

9. A display workstation, comprising:
    a processor;
    a display station operatively coupled with the processor; and
    an interface operatively coupled with the processor, wherein the respective processor and interface are configured to allow a user to selectively cause the processor to
        obtain a plurality of images, each of the images in the plurality having at least one corresponding region,
        generate a synthesized 2D mammography image having the at least one corresponding region, wherein the synthesized 2D mammography image is a synthesized mammography image that is generated by
            selecting an image source from the plurality of images to source image data for the at least one corresponding region in the synthesized 2D mammography image by comparing attributes of the at least one corresponding region in each of the plurality of images to identify the image source having preferred attributes,
        generate a map for a user-selected region in the synthesized 2D mammography image, whereby the map identifies at least one of the plurality of images that sourced the user-selected region in the synthesized 2D mammography image, and
        display on the display station the at least one of the plurality of images that sourced the user-selected region when the user-selected region is selected by the user,
    the interface further configured to allow a user to selectively cause the processor to display three-dimensional information related to a selected region of the synthesized 2D mammography image on the display station.

10. The display workstation of claim 9, wherein the interface includes a mode selection mechanism enabling a user to select a mode of either generation or display of the synthesized 2D mammography image on the display station.

11. The display workstation of claim 9, wherein the interface allows a user to view both of or toggle between the synthesized 2D mammography image and the one of the group of images that sourced the at least one of the plurality of regions.

12. A display workstation, comprising:
    a processor;
    a display station operatively coupled with the processor; and
    an interface operatively coupled with the processor, wherein the interface is configured to allow a user to selectively cause the processor to generate and display a synthesized 2D mammography image on the display station, the synthesized 2D mammography image comprising a two dimensional synthesized image comprising a plurality of regions, wherein at least two of the regions are sourced from different images selected from a group of images, and wherein the group of images include tomosynthesis projection images, tomosynthesis reconstruction slices, mammograms and synthesized 2D images,
    the interface further configured to allow a user to selectively cause the processor to display three-dimensional information related to a selected region of the synthesized 2D mammography image on the display station,
    wherein the interface provides a graphical indicator along with a display of the synthesized 2D mammography image such that the graphical indicator illustrates a depth of attributes within the regions.

13. The display workstation of claim 12, wherein the interface allows a user to cause the processor to display simultaneously, sequentially, or in toggle mode, two or more of the synthesized 2D mammography image, a tomosynthesis projection image, a tomosynthesis reconstruction slice, a mammogram, and a synthesized 2D image.

* * * * *